(12) United States Patent
Vaya et al.

(10) Patent No.: US 8,216,609 B2
(45) Date of Patent: *Jul. 10, 2012

(54) MODIFIED RELEASE COMPOSITION OF HIGHLY SOLUBLE DRUGS

(75) Inventors: Navin Vaya, Gujarat (IN); Rajesh Singh Karan, Gujarat (IN); Sunil Sadanand Nadkarni, Gujarat (IN); Vinod Kumar Gupta, Gujarat (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 1161 days.

This patent is subject to a terminal disclaimer.

(21) Appl. No.: 10/630,348

(22) Filed: Jul. 29, 2003

(65) Prior Publication Data
US 2004/0096501 A1     May 20, 2004

(30) Foreign Application Priority Data

Aug. 5, 2002  (IN) ............ 696/MUM/2002
Aug. 5, 2002  (IN) ............ 698/MUM/2002
Jan. 22, 2003 (IN) ............ 81/MUM/2003

(51) Int. Cl.
*A61K 9/00* (2006.01)
*A61K 9/20* (2006.01)
*A61K 9/22* (2006.01)
*A61K 9/26* (2006.01)

(52) U.S. Cl. ........ 424/469; 424/400; 424/464; 424/465; 424/468

(58) Field of Classification Search .............. None
See application file for complete search history.

(56) References Cited

U.S. PATENT DOCUMENTS

| | | | |
|---|---|---|---|
| 2,566,582 | A | 7/1951 | Rotner |
| 2,968,158 | A | 1/1961 | Ruschig et al. |
| 3,097,242 | A | 7/1963 | Hoehn et al. |
| 3,174,901 | A | 3/1965 | Sterne |
| 3,454,635 | A | 7/1969 | Weber et al. |
| 3,654,357 | A | 4/1972 | Bretschneider et al. |
| 3,668,215 | A | 6/1972 | Plumpe et al. |
| 3,669,966 | A | 6/1972 | Ambrogi |
| 3,708,486 | A | 1/1973 | Kutter, et al. |
| 3,801,495 | A | 4/1974 | Gould |
| 3,957,833 | A | 5/1976 | Chodnekar et al. |
| 4,080,472 | A | 3/1978 | Bohuon |
| 4,363,802 | A | 12/1982 | Matsumura et al. |
| 4,376,777 | A | 3/1983 | Kawamatsu et al. |
| 4,572,912 | A | 2/1986 | Yoshioka et al. |
| 4,725,610 | A | 2/1988 | Meguro et al. |
| 4,775,687 | A | 10/1988 | Meguro et al. |

(Continued)

FOREIGN PATENT DOCUMENTS

EP     0008203 A1     2/1980

(Continued)

OTHER PUBLICATIONS

Merck Index citations niacin, sodium valproate, nicotine.*

(Continued)

*Primary Examiner* — Anand Desai
*Assistant Examiner* — Melissa Mercier
(74) *Attorney, Agent, or Firm* — Hedman & Costigan, P.C.; James V. Costigan

(57) ABSTRACT

A novel modified release dosage form comprising of a high solubility active ingredient, which utilizes dual retard technique to effectively reduce the quantity of release controlling agents; a process for preparing the dosage form.

32 Claims, 5 Drawing Sheets

U.S. PATENT DOCUMENTS

| | | | |
|---|---|---|---|
| 4,791,125 A | 12/1988 | Clark | |
| 4,835,184 A | 5/1989 | Hugelin et al. | |
| 5,002,953 A | 3/1991 | Hindley | |
| 5,061,717 A | 10/1991 | Clark et al. | |
| 5,098,725 A | 3/1992 | Rotman et al. | |
| 5,104,888 A | 4/1992 | Yoshioka et al. | |
| 5,183,823 A | 2/1993 | Sohda et al. | |
| 5,225,426 A | 7/1993 | Miyaoka et al. | |
| 5,232,945 A | 8/1993 | Hulin | |
| 5,264,451 A | 11/1993 | Kees | |
| 5,306,726 A | 4/1994 | Hulin | |
| 5,334,604 A | 8/1994 | Goldstein et al. | |
| 5,399,357 A * | 3/1995 | Akiyama et al. | 424/457 |
| 5,472,704 A * | 12/1995 | Santus et al. | 424/435 |
| 5,478,852 A | 12/1995 | Olefsky et al. | |
| 5,589,492 A | 12/1996 | Haigh | |
| 5,945,125 A | 8/1999 | Kim | |
| 6,031,004 A | 2/2000 | Timmins et al. | |
| 6,048,883 A | 4/2000 | Haigh et al. | |
| 6,296,874 B1 | 10/2001 | Cutie | |
| 6,337,091 B1 | 1/2002 | Kim et al. | |
| 6,340,475 B2 | 1/2002 | Shell et al. | |
| 6,600,300 B2 * | 7/2003 | Groeneveld et al. | 323/282 |
| 6,660,300 B1 * | 12/2003 | Timmins et al. | 424/469 |
| 6,790,459 B1 | 9/2004 | Cheng et al. | |
| 6,866,866 B1 | 3/2005 | Chen et al. | |
| 2004/0022849 A1 | 2/2004 | Castan et al. | |

FOREIGN PATENT DOCUMENTS

| | | |
|---|---|---|
| EP | 0155845 A1 | 9/1985 |
| EP | 0332332 A1 | 9/1989 |
| EP | 0428312 A2 | 5/1991 |
| EP | 0533933 A1 | 3/1993 |
| EP | 0842925 A1 | 5/1998 |
| WO | WO 92/18501 | 10/1992 |
| WO | WO 93/02079 | 2/1993 |
| WO | WO 93/22445 | 11/1993 |
| WO | WO 94/05659 | 3/1994 |

OTHER PUBLICATIONS

Merck Index citations for Niacin, sodium valproate, nicotine.*

Merck Index Online: accessed Aug. 4, 2008 for Niacin, Sodium Valproate, and nicotine.*

Brophy et al, "Influence of Coating and Core Modifications on the In-vitro Release of Methylene Blue from Ethylcellulose Microcapsules Produced by Pan Coating Procedure"; J. Pharm Pharmacol; 1981; pp. 495-499, No. 33.

Perumal et at, "Effect of Formulation Variables on In-vitro Drug Release and Micromeritic Properties of Modified Release Ibuprofen Microspheres"; 1999; pp. 4, 475-487; No. 16.

* cited by examiner

MODIFIED RELEASE COMPOSITION OF HIGHLY SOLUBLE DRUGS

This application claims the priority of Indian Patent Applications 698/MUM/2002, filed Aug. 5, 2002; 696/MUM/2002, filed Aug. 5, 2002 And 81/MUM/2003, filed Jan. 22, 2003.

FIELD OF INVENTION

This invention relates to a modified release dosage form comprising of a high solubility active ingredient, which utilizes dual retard technique to effectively reduce the quantity of release controlling agents; a process for preparing the formulation.

BACKGROUND OF THE INVENTION

It is well known to those skilled in the art that the blood levels of drugs need to be maintained above a minimum effective level and below its minimum toxic level in order to obtain the desired therapeutic effects and to minimize side effects. Unfortunately, the pharmacokinetic properties (absorption, elimination and metabolism) of most drugs are such that they need to be administered three to four times a day. This kind of a dosing regimen is very inconvenient and leads to reduction in patient compliance. Reduction of dosing regimen from three times a day (t.i.d.) to twice daily (b.i.d.) to once a day results in increased convenience and comfort and therefore increased patient compliance. Drugs that are administered in the form of conventional tablets of capsules become available to body fluids at a rate that is initially very high, followed by a rapid decline. For many drugs, this delivery pattern results in a transient overdose, followed by a long period of under dosing. This is a pattern of limited clinical usefulness. The delivery pattern was improved in the 1970's with the introduction of a variety of modified delivery systems. Modified release formulations, which are effective in maintaining the therapeutic blood levels over, extended periods of time result in optimal therapy. They not only reduce the frequency of dosing, but they also reduce the severity and frequency of side effects, as they maintain substantially constant blood levels and avoid the fluctuations associated with the conventional immediate release formulations administered three to four times a day.

There are a number of different modified release dosage forms available commercially. However, some of these are expensive to manufacture and can be difficult to swallow, particularly in elderly patients. Many of these modified delivery systems utilize hydrophilic, polymeric matrices that provide useful levels of control to the delivery of sparingly soluble drugs. For soluble drugs, however, and particularly for highly soluble drugs, such matrices do not provide adequate control over the release rate, instead resulting in a release that approximates first-order kinetics and may have a problem of dose dumping or burst release. However, since many modified release dosage forms contain comparatively large amounts of active ingredient it is often necessary to include large amounts of suitable excipients to achieve appropriate controlled release profiles. Clearly, this will tend to increase the size of the dosage form.

The various techniques to make modified release dosage form of drugs as described in prior art are as follows— method of prolonging the release of a highly water-soluble drug is disclosed PCT Patent application no. WO99/47128. A biphasic controlled release delivery system for metformin hydrochloride, which has prolonged gastric residence and that swells following hydration. The ratio of inner solid phase to outer continuous phase is 0.5:1 to about 4:1. The major limitation of this invention is that it provides a very bulky formulation for higher doses of the metformin hydrochloride that is very inconvenient for human consumption. For instance, example cited provides formulation of 500 mg metformin hydrochloride with tablet weight of 1.0 gm. Hence restricting to the low dose sustained release tablets of 500 mg or slightly more and making it obligatory to take two tablets of 500 mg each time to provide sustain action. The cited example teaches use of combination of atleast one hydrophilic polymer and which is a essential part for swelling. Non swellable or nonerodeble formulations are not included in the invention.

PCT application No. WO 02/28181 Al describes a monolithic sustained release formulation of metformin hydrochloride. The method of making the formulation involves hot melt granulation followed by wet granulation with binders or extrusion. The formulation essentially requires binder and auxiliary pharmaceutically acceptable excipients. The formulation consists of metformin hydrochloride polymer and or hydrophobic material. The dosage form release more than 90% of the drug within 8 hours.

Similarly U.S. Pat. No. 6,340,475 B2 assigned to Depomed Inc. describes monolithic controlled release formulation of highly water soluble drugs including metformin hydrochloride. The formulation swells when ingested thus prolonging its residence time in the stomach. The formulations are made of hydrophilic polymers, which results in swellable and erodible matrix.

Another method of prolonging the release of a highly water-soluble drug is disclosed in International Patent application publication no. WO 96/26718, published Sep. 6, 1996. The method of this publication is the incorporation of the drug into a polymeric matrix to form a tablet that is administered orally. The polymer is water-swellable yet erodible in gastric fluids.

Similarly Chih-Ming Chen in international patent application number WO 02/36100 describes a once a formulation of metformin hydrochloride which is based on osmotically controlled technique and that is non expandable in nature and has a passage in the coating membrane for release of drug.

Kim et al. in U.S. Pat. No. 6,337,091 describes a matrix based controlled release formulation for highly soluble drugs over long periods of time. The release controlling agent is a swellable gum which encapsulates or make granules of drug, which is then disposed in more swellable erodible polymers such as HPMC or poly(ethyleneoxide).

These systems can provide for modified release for selected active ingredients like active ingredients with low dose or low water solubility. However, when a highly soluble or high dose active ingredient is used, most of these systems have the disadvantages such as comparatively low payload of active ingredient thus making dosage form bulky and expensive or lead to burst effect or prolonged release of active ingredient for a shorter duration or use of complex manufacturing procedure and/or equipment.

There exists a need for compositions and process for making orally deliverable dosage form containing highly soluble active ingredient as modified release that overcomes the problems discussed above. This invention addresses the need.

Therefore, it would be of considerable clinical benefit to design a dosage form with high pay load of highly soluble active ingredient that would be much easier for the patient to swallow. This type of technology could also be used to reduce the size of many existing drug formulations.

Therefore an object of the present invention is a modified release dosage form of high solubility active ingredient.

The second object of the present invention is a modified release dosage form with high payload of active ingredient, which is suitable for swallowing for humans.

Yet another object of the present invention is to provide a dosage form, which uses dual retard technique to control the release of the high solubility active ingredient and significantly reduce the amount of release controlling agents which are otherwise required in very high quantity and make the dosage form very bulky and therefore pose difficulty in swallowing.

A further object of the present invention is to provide a dosage form, which gives accurate dosing and is simple to prepare.

A further object of the present invention is to provide a dosage form, which can be given twice a day or more preferably can be given once a day.

SUMMARY OF THE INVENTION

The above objects are realized by a dosage form, which comprises of a) Micro matrix particles containing high solubility active ingredient and one or more hydrophobic release controlling agent, b) Coating of Micro matrix particles with one or more hydrophobic release controlling agents. It may optionally also include one or more commonly used excipients in oral pharmaceutical formulations. The present invention also provides solid oral dosage form comprising a composition according to the invention.

The present invention also teaches the use of dual retard technique to effectively control the release rate of modified release active ingredient by using small quantity of release controlling agents. This dual retard technique thus sufficiently reduces the size of the dosage form, which is convenient for swallowing.

The present invention further teaches the use of hydrophobic release controlling agents.

The present invention also provides a novel process for preparing the novel formulations of the invention.

The present invention further provides a method of treating an animal, particularly a human in need of treatment utilizing the active agents, comprising administering a therapeutically effective amount of composition or solid oral dosage form according to the invention to provide administration of active ingredients.

DETAILED DESCRIPTION OF THE INVENTION

This invention relates to a modified release dosage form comprising of a high solubility active ingredient prepared by using dual retard technique to control the release of the high solubility active ingredient and to increase the payload of high solubility active ingredient The term "modified release" as used herein in relation to the composition according to the invention or a rate controlling polymer or used in any other context means release, which is not immediate release and is taken to encompass controlled release, sustained release, prolonged release, timed release, retarded release, extended release and delayed release. The term "modified release dosage form" as used herein can be described as dosage forms whose drug-release characteristics of time course and/or location are chosen to accomplish therapeutic or convenience objectives not offered by conventional dosage forms such as a solution or an immediate release dosage form. Modified release solid oral dosage forms include both delayed and extended release drug products (as per US FDA guideline for 'SUPAC-MR: Modified Release Solid Oral Dosage Forms').

The term "dosage form" denotes any form of the formulation that contains an amount sufficient to achieve a therapeutic effect with a single administration.

The term "active ingredient" refers to an agent, active ingredient compound or other substance, or compositions and mixture thereof that provide some pharmacological, often beneficial, effect. Reference to a specific active ingredient shall include where appropriate the active ingredient and it's pharmaceutically acceptable salts.

The term "high solubility" as used herein in relation to active agent means that from less than 1 part to 30 parts of water will be required to dissolve 1 part of active ingredient.

The invention provides a novel modified release dosage form of high solubility active ingredient, which utilizes dual retard technique to effectively reduce the quantity of release controlling agents and a process for preparing the dosage form.

The dosage form comprises of a) Micro matrix particles containing, high solubility active ingredient and one or more hydrophobic release controlling agent, b) Coating of Micro matrix particles with one or more hydrophobic release controlling agents. It may optionally also include one or more commonly used excipients in oral pharmaceutical formulations. The release of high solubility active ingredient is controlled through dual retard technique. The dual retard technique is a combination of matrix formulations and reservoir formulations. First the micromatrix particles of high solubility dose active ingredient and one or more hydrophobic release controlling agents are formed and then these are further coated with one or more release controlling agents. Thus the dual retard release technique presents the double barriers and effectively controls the diffusion of the high solubility active ingredients from the present invention in predictable manner and also significantly reduces the amount of release controlling agents which are otherwise required in very high quantity and make the dosage form very bulky and therefore pose difficulty in swallowing. The other advantages of the present invention are such as it reduces the chances of dose dumping, unnecessary burst effects and failure of the system, which are otherwise usually associated with simple matrix or reservoir systems.

The high solubility active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, high solubility active ingredient, where applicable, may be present either in the form of one substantially optically pure enantiomer or as a mixture of enantiomers or polymorphs thereof.

The high solubility active ingredients comprises of the following therapeutic classes but not limited to antidiabetics, anti-histamines, anti-depressants, anti-viral agents, anesthetics, antacids, anti-arthritis, antibiotics, anti-psychotics, antispasmodics, anxiolytic agents, appetite suppressants, cardiovascular agents, cough suppressants, emollients, gastrointestinal agents, growth regulators, respiratory stimulants, vitamins, angiotensin converting enzyme inhibitors, anti-asthmatics, anti-cholesterolemics, anti-convulsants, anti-depressants, anti-diarrhea preparations, anti-infective, anti-inflammatory agents, anti-nauseants, anti-stroke agents, anti-tumor drugs, anti-tussives, anti-uricemic drugs, amino-acid preparations, antiemetics, antiobesity drugs, antiparasitics, antipyretics, appetite stimulants, cerebral dilators, chelating agents, cholecystokinin antagonists, cognition activators, deodorants, dermatological agents, diuretics, erythropoietic drugs, fertility agents, synthetic hormones, laxatives, mineral supplements, neuroleptics, neuromuscular agents, peripheral vaso-dilators, prostaglandins, vaginal preparations, vasoconstrictors, vertigo agents, biguanides, sulphonylurease, meglitinides, PPAR gama agonist [insulin sensitisers (thiazolidinedione)], alpha-glucosidase inhibitors and the active ingredients described in U.S. Pat. Nos. 2,968,158, 3,097,242, 3,454,635, 3,654,357, 3,668,215, 3,669,966, 3,708,486, 3,801,495, 5,104,888, 5,232,945, 5,264,451, 5,478,852, 6,296,874, 3,957,853, 4,080,472, 3,174,901, 4,835,184, 6,031,004 and European patent publication numbers EP0008203, EP0032128, EP0139421, EP0155845, EP0177353, EP0208420, EP0257881, EP0306228, EP0319189, EP0332331, EP0332332, EP0428312, EP0489663, EP0508740, EP0528734, EP0533933, EP0833933, EP87112480.6 and Japanese patent number 05271204 and United Kingdom patent numbers 5504078, GB2088365A and PCT patent application numbers WO91/19702, WO92/03425, WO92/18501, WO93/02079, WO93/21166, WO93/22445, WO94/01420, WO94/05659.

Examples of high solubility active ingredients comprises of but not limited to metformin hydrochloride, phenformin, buformin, captopril, ranitidine hydrochloride, potassium chloride, clindamycin, hydroxyurea, erythromycin lactobionate, vancomycin hydrochloride, balsalazide disodium, aminocaproic acid, lisinopril, tramadol, acetaminophen, ciprofloxacin, esters of ampicillin, sodium valproate, niacin, diltiazem, venlafaxine, isosorbide 5-imononitrate, isosorbide dinitrate, pentoxyphylline, propranolol, quetiapine. Other drugs suitable for use and meeting the solubility criteria described above will be apparent to those skilled in the art.

The quantity of the high dose, high solubility active ingredient for e.g. as mentioned above can be less than or equal to 1500 mg.

A dosage form of the present invention may optionally contain more than one high solubility active ingredient.

A dosage form of the present invention may optionally contain more than one antidiabetic active ingredient.

As indicated above the outer portion of the present invention may comprise auxiliary excipients such as for example lubricants, plasticisers, anti-tack agents, opacifying agents, pigments, and such like. As will be appreciated by those skilled in the art, the exact choice of excipient and their relative amounts will depend to some extent on the final oral dosage form.

Suitable lubricants, including agents that act on the flowability of the powder to be compressed are, for example, colloidal slilcon dioxide such as Aerosil 200 (Aerosil is a Trade Mark); talc; stearic acid, magnesium stearate, calcium stearate and sodium stearyl fumarate.

In micro matrix particles, the active ingredient and one or more hydrophobic release controlling agents are preferably present in a ratio of from 100:1 to 100:75, more particularly from 100:2.5 to 100:50, still more preferably from 100:2.5 to 100:30 and most preferably from 100:2.5 to 100:20.

Micro matrix particles and coating of one or more hydrophobic release controlling agents are preferably present in a ratio of from 100:0.5 to 100:75, more particularly from 100:2.5 to 100:50, still more preferably from 100:2.5 to 100:30 and most preferably from 100:2.5 to 100:20.

According to one embodiment the release controlling agents are pharmaceutically excipients, which are hydrophobic in nature.

The polymers that can be used to form the rate-controlling membrane or micromatrix are described in greater detail herein below.

The hydrophobic release controlling agents are selected from but are not limited to Ammonio methacrylate copolymers type A and B as described in USP, methacrylic acid copolymer type A, B and C as described in USP, Polyacrylate dispersion 30% as described in Ph. Eur., Polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly (hexyl methacrylate). Poly(isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil.

According to an especially preferred embodiment the release controlling agent contains ammonio methacrylate co-polymers and fatty acid esters as hereinafter described.

The suitable hydrophobic agents are polymers sold under the Trade Mark EUDRAGIT RS® (Ammonio Methacrylate Copolymer type B USP), EUDRAGIT NE 30D®(Polyacrylate dispersion 30% Ph., Eur.),EUDRAGIT RL® (Ammonio Methacrylate Copolymer type A USP) and KOLLICOAT SR 30 D® and fatty acid esters such as glyceryl behenate, and hydrogenated castor oil. EUDRAGIT® polymers are polymeric lacquer substances based on acrylate and/or methacrylates.

The dosage form can also include one or more commonly used excipients in oral pharmaceutical formulations.

Representative commonly used excipients in oral pharmaceutical formulations include talc, fumed silica, glyceryl monostearate, magnesium stearate, calcium stearate, kaolin, colloidal silica, gypsum, Tween 80, Geleol pastiles (trade mark), micronised silica and magnesium trisilicate.

The quantity of commonly used excipients in oral pharmaceutical formulations used is from about 2% to about 500% by weight, preferably from 2 to 100% more particularly 10 to 60% based on the total dry weight of the polymer.

The dosage form can also include a material that improves the processing of the release controlling agents. Such materials are generally referred to as "plasticisers" and include, for example, adipates, azelates, benzoates, citrates, isoebucaes, phthalates, sebacates, stearates, tartrates, polyhydric alcohols and glycols.

Representative plasticisers include acetylated monoglycerides; butyl phthalyl butyl gylcolate; dibutyl tartrate; diethyl phthalate; dimethyl phthalate,; ethyl phthalyl ethyl glycolate; glycerin; ethylene glycol, propylene glycol; Triethyl citrate; triacetin; tripropinoin; diacetin; dibutyl phthalate; acetyl monoglyceride; polyethylene glycols; castor oil; triethyl citrate; polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylexyl phthalate, di-n-octyl phthalate, di-I-octyl phthalate, di-I-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate, glyceryl monocaprate, nicotine, oxybutamine chloride, perinodopril erbumine, pilocorpine, poldine methyl sulfate and zalcitane.

The amount of plasticiser to be used is from about 1% to 50% based on the weight of the dry release controlling agent(s).

The amount of release controlling agent(s) to be used in forming the outer portion will be determined based on various parameters such as the desired delivery properties, including the amount of active ingredient to be delivered, the active ingredient release rate desired, and the size of the micro matrix particles.

The novel modified release dosage form of the present invention can be manufactured by the following procedure:

The micro matrix particles can be manufactured in accordance with usual techniques in which the active ingredient and one or more hydrophobic release controlling agents are mixed and granulated by adding solvent in a low or high shear mixer or by fluidized bed granulator. The granulate is dried, preferably in a fluidized bed dryer. The dried granulate is sized. The sizing of the micromatrix particles can be done using oscillating granulator, comminuting mill or any other conventional method. The sieve used for the sizing can have openings from 0.25 mm to 5 mm. Alternatively the micro matrix particles can be made by extrusion, spheronization or by roller compaction. The micro matrix particles can be coated by a solution of one or more hydrophobic release controlling agents by any known method, including spray application. Spraying can be carried out using a fluidized bed coated (preferably Wurster coating), or in a pan coating system. Alternatively the coating of the micro matrix particles with one or more rate controlling agents can be done by hot melt process using a granulator or fluidized bed coated (preferably Wurster coating), or in a pan coating system. The compression of tablets is carried out on usual compression machines (e.g. machines of the Manesty, Cadmach or Kilian). The tablets can be made of various sizes and shapes.

DESCRIPTION OF PREFERRED EMBODIMENTS

Figure 1A:
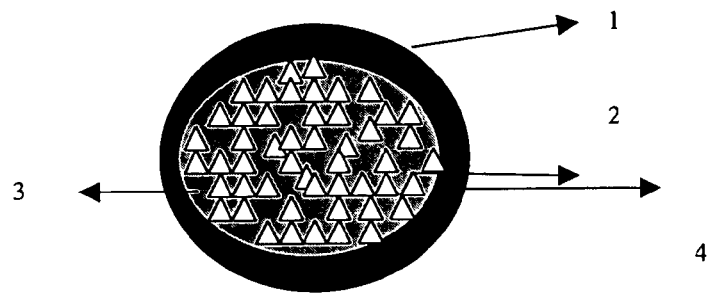
FIG. 1(a) is a cross section of coated micro matrix particles prepared by spheronization and coating for the purpose of illustration only.
Figure 1B:
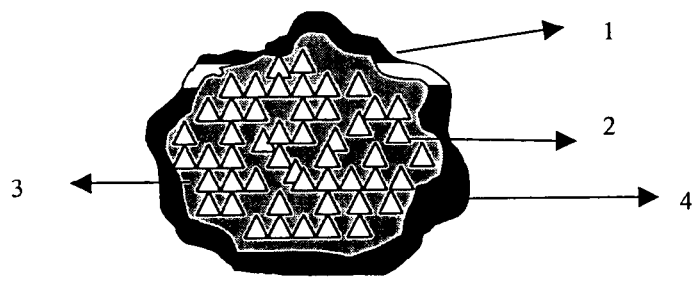
FIG. 1(b) is a cross section of coated micro matrix particles prepared by granulation and coating for the purpose of illustration only.
Figure 2:
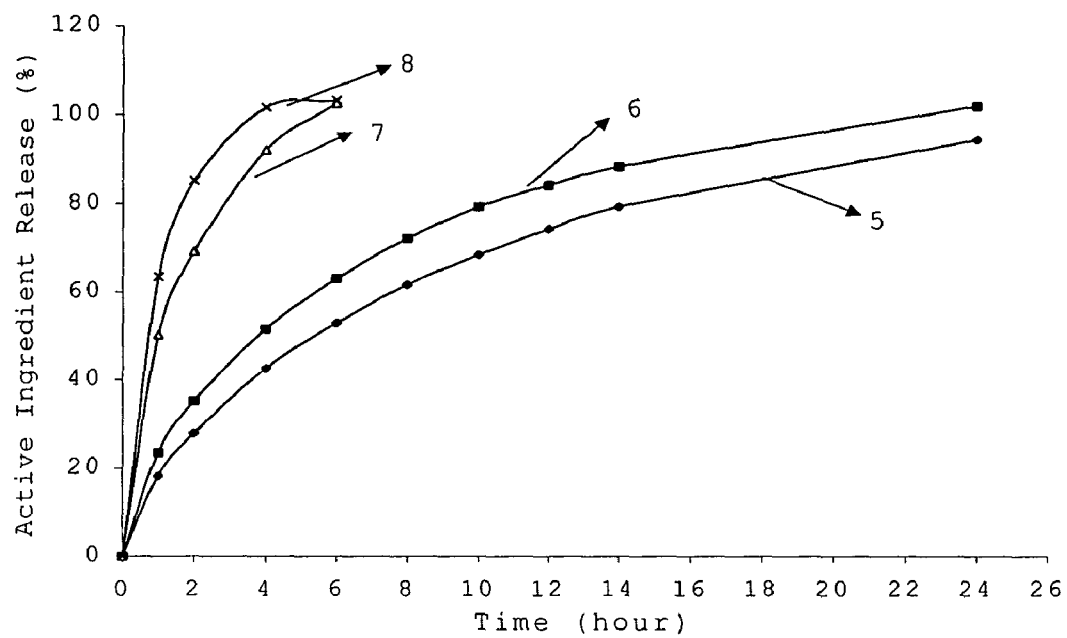
FIG. 2 is a plot of % active ingredient versus time for modified release active agent prepared using dual retard technique as described in the present invention and prepared without retard release technique as per examples 1 and 3.
Figure 3:
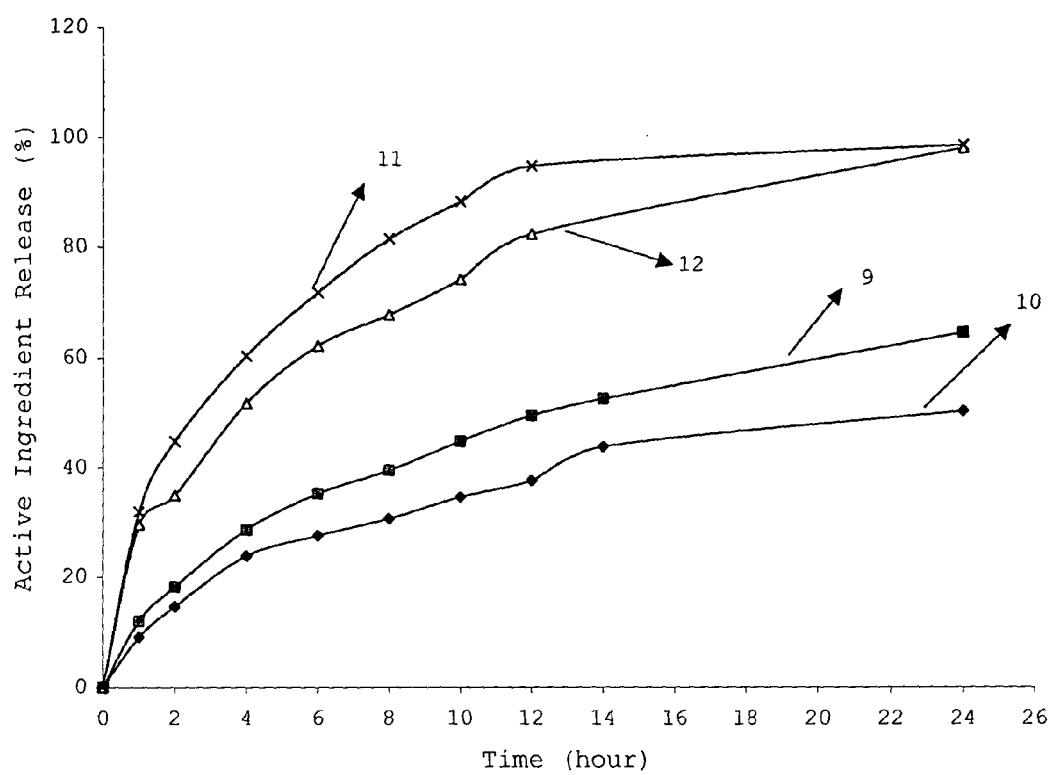
FIG. 3 is a plot of % active ingredient versus time for modified release active agent prepared using dual retard technique as described in the present invention and prepared without retard release technique as per examples 2 and 4.
Figure 4:
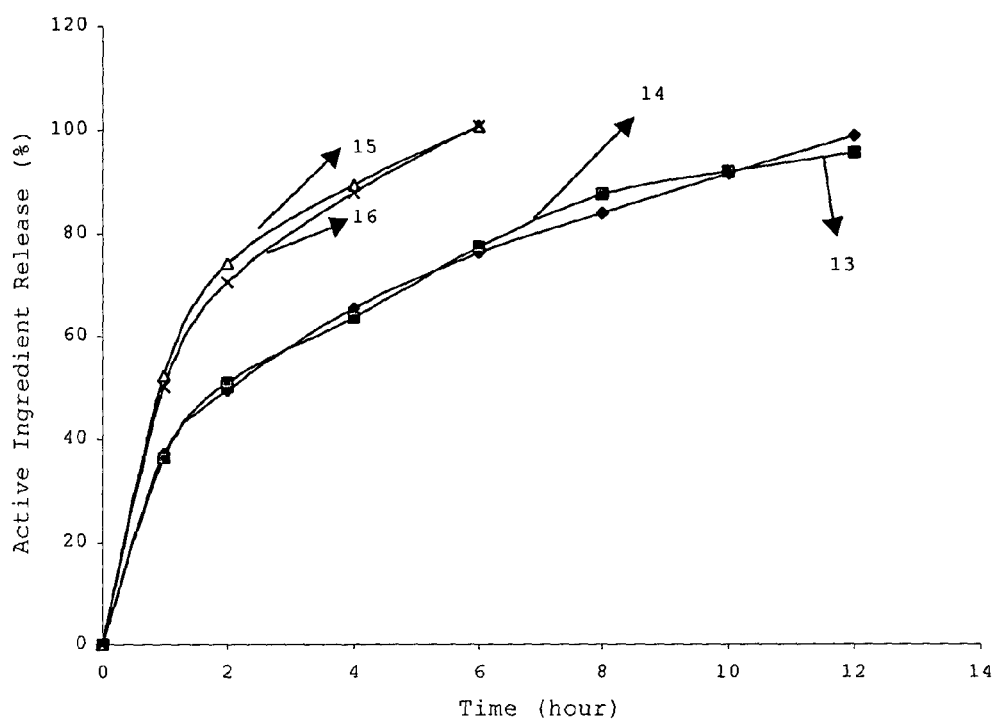
FIG. 4 is a plot of % active ingredient versus time for modified release active agent prepared using dual retard technique as described in the present invention and prepared without retard release technique as per examples 8 and 11 respectively.

FIGS. 1(a) and 1(b) show the cross section of the coated micro matrix particles 1 as described in the present invention and having a high solubility active ingredient 2, hydrophobic release controlling agent 3 and a coating of hydrophobic release controlling agent 4. FIGS. 2 and 3 show release of high solubility active agent 5 & 6 and 9 & 10 as per example 1 & 2 respectively from a dosage form prepared using dual retard technique and release of high solubility active agent 7 & 8 and 11 & 12 as per example 3 & 4 respectively from a dosage form prepared without using dual retard release technique. The total quantity of the hydrophobic release controlling agent is same in all the dosage forms inspite of that the figures clearly shows that dual retard technology significantly reduces the burst effect and effectively controls the release rate of the high solubility active ingredient for prolonged period. FIG. 4 shows release of high solubility active agent 13 & 14 as per example 8 from a dosage form prepared using dual retard technique and release of high solubility active agent 15 & 16 as per example 11 from a dosage form prepared without using dual retard release technique. The total quantity of the hydrophobic release controlling agent is same in all the dosage forms. Inspite of that the figures clearly show that dual retard technology significantly reduces the burst effect and effectively controls the release rate of the high solubility antidiabetic active ingredient for prolonged period.

The following examples further illustrate but by no means limit the present invention.

The dissolution of novel dosage form of the present invention was determined by following method.

For sodium valproate—
Instrument—Apparatus I, USP (basket)
Revolution—60/min.
Temperature—37±0.5° C.
Dissolution medium—1000 ml pH 6.8 buffer
For niacin—
Instrument—Apparatus I, USP (Basket)
Revolution—100/min.
Temperature—37±0.5° C.
Dissolution medium—900 ml 0.1 N HCl
For venlafaxine hydrochloride—
Instrument—Apparatus II, USP (Paddle)
Revolution—100/min.
Temperature—37±0.5° C.
Dissolution medium—500 ml water
For metformin hydrochloride—
Instrument—Apparatus II, USP (Paddle)
Revolution—50/min.
Temperature—37±0.5° C.
Dissolution medium—900 ml 0.1 N HCl The dissolution of high dose high solubility ingredient of the formulation of the present invention is achieved not more than 50% in 1 hour and from 25 to 90% in six hours.

The dissolution of metformin hydrochloride is achieved not more than 50% in 1 hour, and from 30 to 90% is in four hours and not less than 65% in 12 hours.

After oral administration of a dosage form of the present invention the maximum plasma concentration can be achieved between 700 ng/ml and 2500 ng/ml, preferably from 900 ng/ml to 2400 ng/ml and more preferably from 1000 ng/ml to 2350 ng/ml. The invivo mean dissolution time (MDT) of the dosage form of the present invention is approximately 4 to 6 hours. The minimum plasma concentration (at 24 hours) of the said dosage form ranges between 0 and 450 ng/ml after oral administration.

The composition of the micromatrix particles and coated micromatrix particles of the dosage form comprising niacin is as follows—
Micro matrix particles—
    Niacin 75% w/w to 99% w/w
    EUDRAGIT RS® 1% w/w to 25% w/w.
Coated micro matrix particles
    Micro matrix particles 70% w/w to 99% w/w
    Hydrogenated castor oil 1% w/w to 30% w/w
    Magnesium stearate 0% w/w to 2% w/w The composition of the micromatrix particles and coated micromatrix particles of the dosage form comprising metformin hydrochloride is as follows—
Micro matrix particles—
    Metformin hydrochloride 75% w/w to 99% w/w
    EUDRAGIT RS® 1% w/w to 25% w/w
Coated micro matrix particles
    Micro matrix particles 70% w/w to 99% w/w
    Hydrogenated castor oil 1% w/w to 30% w/w
    Magnesium stearate 0% w/w to 2% w/w

EXAMPLES

Example 1

A) Micro matrix particles—90.91% w/w of sodium valproate is mixed with 9.09% w/w of EUDRAGIT RS® (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of tablets

Tablet (1)—1286 mg granules are pressed to tablet (equivalent to 1000 mg sodium valproate) using 20.3×9.8 mm oval punches.

Tablet (2)—643 mg granules are pressed to tablet(equivalent to 500 mg sodium valproate) using 14.95×8.35 mm oblong punches.

The dissolution rate of the novel dosage form was determined (Table 1)

TABLE 1

| | Dissolution profile | |
|---|---|---|
| Time | % Released | |
| (hour) | Tablet (1) | Tablet (2) |
| 1 | 18.2 | 23.4 |
| 2 | 27.8 | 35.1 |
| 4 | 42.5 | 51.5 |
| 6 | 52.8 | 62.9 |
| 8 | 61.6 | 72.1 |
| 10 | 68.3 | 79.2 |
| 12 | 74.2 | 84.1 |
| 14 | 79.2 | 88.3 |
| 24 | 94.4 | 102.0 |

Example 2

A) Micro matrix particles—90.91% w/w of niacin is mixed with 9.09% w/w of EUDRAGIT RS® (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of tablets

Tablet (1)—1286 mg granules are pressed to tablet (equivalent to 1000 mg niacin) using 20.3×9.8 mm oval punches.

Tablet (2)—643 mg granules are pressed to tablet (equivalent to 500 mg niacin) using 14.95 X 8.35 mm oblong punches.

The dissolution rate of the novel dosage form was determined (Table 2)

TABLE 2

| | Dissolution profile | |
|---|---|---|
| Time | % Released | |
| (hour) | Tablet (1) | Tablet (2) |
| 1 | 9.1 | 12.0 |
| 2 | 14.6 | 18.2 |
| 4 | 23.8 | 28.6 |
| 6 | 27.5 | 35.2 |
| 8 | 30.6 | 39.5 |
| 10 | 34.7 | 44.8 |
| 12 | 37.6 | 49.5 |
| 14 | 43.8 | 52.5 |
| 24 | 50.3 | 64.5 |

Dosage forms described in the examples 3 and 4 are prepared by not coating the micro matrix particles but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 3

77.76% w/w of sodium valproate is mixed 7.78% w/w of EUDRAGIT RS® (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of tablets

Tablet (1)—1286 mg granules are pressed to tablet (equivalent to 1000 mg sodium valproate) using 20.3×9.8 mm oval punches.

Tablet (2)—643 mg granules are pressed to tablet (equivalent to 500 mg sodium valproate) using 14.95×8.35 mm oblong punches.

The dissolution rate of the novel dosage form was determined (Table 3)

TABLE 3

| Time | % Released | |
|---|---|---|
| (hour) | Tablet (1) | Tablet (2) |
| 1 | 63.4 | 50.2 |
| 2 | 85.1 | 69.1 |
| 4 | 101.6 | 92.0 |
| 6 | 103.1 | 102.5 |

Dissolution profile

Example 4

77.76% w/w of niacin is mixed with 7.78% w/w of EUDRAGIT,RS® (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of tablets

Tablet (1)—The granules are pressed to 1286 mg (equivalent to 1000 mg niacin) are compressed using 20.3×9.8 mm oval punches.

Tablet (2)—The granules are pressed to 643 mg (equivalent to 500 mg niacin) are compressed using 14.95×8.35 mm oblong punches.

The dissolution rate of the novel dosage form was determined (Table 4)

TABLE 4

Dissolution profile

| Time | % Released | |
|---|---|---|
| (hour) | Tablet (1) | Tablet (2) |
| 1 | 31.9 | 29.6 |
| 2 | 44.8 | 34.9 |
| 4 | 60.3 | 51.7 |
| 6 | 71.7 | 62.1 |
| 8 | 81.4 | 67.7 |
| 10 | 88.2 | 74.7 |
| 12 | 94.7 | 82.3 |
| 24 | 98.6 | 98.1 |

Example 5

A) Micro matrix particles—80.93% w/w of venlafaxine hydrochloride is mixed with 19.07% w/w of EUDRAGIT RS® (Ammonio Methacrylate Copolymer type B USP) and the mixture is granulated with a solvent mixture of acetone and methylene chloride and then dried. The granules are sized.

B) Coating of Micro matrix particles—70.13% w/w of micro matrix particles is charged in fluidized bed processor. 28.37% w/w of hydrogenated castor oil is dissolved in acetone and this coating solution is sprayed to coat the micro matrix particles. The coated micro matrix particles are sieved and mixed with 1.0% w/w magnesium stearate and 0.50% w/w colloidal silicon dioxide.

C) Compression of tablets—299.09 mg granules are pressed to tablet (equivalent to 150 mg venlafaxine) 9.53 mm round, concave punches.

The dissolution rate of the novel dosage form was determined (Table 5)

TABLE 5

Dissolution profile

| Time (hour) | % Released |
|---|---|
| | 32.1 |
| 4 | 41.8 |
| 6 | 50.3 |
| 8 | 62.5 |
| 12 | 68.4 |

Example 6

A) Micro matrix particles—95.24% w/w of niacin is mixed with 4.76% w/w of EUDRAGIT RS® (Ammonio Methacrylate Copolymer type B USP) and the mixture is granulated solvent mixture of acetone and methylene chloride and then dried. The granules are sized.

B) Coating of Micro matrix particles—92.43% w/w of micro matrix particles is charged in fluidized bed processor. 6.60% w/w of hydrogenated castor oil is dissolved in acetone and this coating solution is sprayed to coat the micro matrix particles. The coated micro matrix particles are sieved and mixed with 0.97% w/w magnesium stearate.

C) Compression of tablets—1136 mg granules are pressed to tablet (equivalent to 1000 mg niacin) using 20.3×9.8 mm oval punches.

The dissolution rate of the novel dosage form was determined (Table 6)

TABLE 6

Dissolution profile

| Time (hour) | % Released |
|---|---|
| 1 | 24.87 |
| 2 | 35.25 |
| 4 | 48.71 |
| 6 | 57.80 |
| 8 | 64.61 |
| 10 | 72.22 |
| 12 | 77.20 |

Example 7

A) Micro matrix particles—Same as example 6.

B) Coating of Micro matrix particles—90.44% w/w of micro matrix particles is charged in fluidized bed processor. 8.61% w/w of hydrogenated castor oil is dissolved in acetone and this coating solution is sprayed to coat the micro matrix particles. The coated micro matrix particles are sieved and mixed with 0.95% w/w magnesium stearate.

C) Compression of tablets—1161 mg granules are pressed to tablet (equivalent to 1000 mg niacin) using 20.3×9.8 mm oval punches.

The dissolution rate of the novel dosage form was determined (Table 7)

TABLE 7

Dissolution profile

| Time (hour) | % Released |
|---|---|
| 1 | 24.35 |
| 2 | 36.41 |
| 4 | 43.86 |
| 6 | 50.63 |
| 8 | 57.43 |
| 10 | 63.82 |
| 12 | 71.20 |

Example 8

A) Micro matrix particles—90.91% w/w of metformin hydrochlotide is mixed with 9.09% w/w of EUDRAGIT RS® (Ammonio Methacrylate Copolymer type B USP)and the mixture is granulated with a solirent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

C) Compression of tablets

Tablet (1)—1286 mg granules are pressed to tablet (equivalent to 1000 mg metformin hydrochloride) are compressed using 20.3×9.8 mm oval punches.

Tablet (2)—643 mg granules are pressed to tablet (equivalent to 500 mg metformin hydrochloride) are compressed using 14.95×8.35 mm oblong punches.

The dissolution rate of the novel dosage form was determined (Table 8)

TABLE 8

Dissolution profile

| Time (hour) | % Released | |
|---|---|---|
| | Tablet (1) | Tablet (2) |
| 1 | 37.1 | 36.5 |
| 2 | 49.5 | 51.0 |
| 4 | 65.3 | 63.6 |
| 6 | 76.2 | 77.5 |
| 8 | 84.0 | 87.8 |
| 10 | 91.7 | 91.9 |
| 12 | 98.9 | 95.8 |

Example 9

A) Micro matrix particles—90.91% w/w of metformin hydrochloride is mixed with 9.09% w/w of EUDRAGIT RS® (Ammonio Methacrylate Copolymer type B USP) and the mixture is granulated with a solvent mixture of acetone and methylene chloride and then dried. The granules are sized.

B) Coating of Micro matrix particles—83.91% w/w of micro matrix particles is charged in fluidized bed processor. 15.26% w/w of hydrogenated castor oil is dissolved in acetone and this coating solution is sprayed to coat the micro matrix particles. The coated micro matrix particles are sieved and mixed with 0.84% w/w magnesium stearate.

C) Compression of tablets 1311 mg granules are pressed to tablet (equivalent to 1000 mg metformin hydrochloride) using 20.3×9.8 mm oval punches.

The dissolution rate of the novel dosage form was determined (Table 9)

TABLE 9

Dissolution profile

| Time (hour) | % Released |
|---|---|
| 1 | 33.44 |
| 2 | 45.79 |
| 4 | 55.28 |
| 6 | 60.45 |
| 8 | 66.10 |
| 10 | 69.87 |
| 12 | 73.88 |
| 24 | 86.97 |

Example 10

A) Micro matrix particles—90.91% w/w of metformin hydrochloride is mixed with 9.09% w/w of EUDRAGIT RS® (Ammonio Methacrylate Copolymer type B USP) and the mixture is granulated with a solvent mixture of acetone and methylene chloride and then dried. The granules are sized.

B) Coating of Micro matrix particles—87.23% w/w of micro matrix particles is charged in fluidized bed processor. 11.90% w/w of hydrogenated castor oil is dissolved in acetone and this coating solution is sprayed to coat the micro matrix particles. The coated micro matrix particles are sieved and mixed with 0.87% w/w magnesium stearate.

C) Compression of tablets 1261 mg granules are pressed to tablet (equivalent to 1000 mg metformin hydrochloride) using 20.3×9.8 mm oval punches.

The dissolution rate of the novel dosage form was determined (Table 10)

TABLE 10

Dissolution profile

| Time (hour) | % Released |
|---|---|
| 1 | 42.1 |
| 2 | 51.30 |
| 4 | 66.60 |
| 6 | 78.80 |
| 8 | 84.60 |
| 10 | 91.00 |
| 12 | 99.70 |

Dosage forms described in the example 11 are prepared by not coating the micro matrix particles but the hydrophobic release controlling agent is mixed with the micro matrix particles. The sole purpose of these examples is to demonstrate the usefulness of the present invention as described earlier. The examples clearly show that the rate of release of the modified release antidiabetic active ingredient is significantly faster than the present invention.

Example 11

77.76% w/w of metformin hydrochloride is mixed with 7.78% w/w of EUDRAGIT RS® (Ammonio Methacrylate Copolymer type B USP) and the mixture is granulated with a solvent mixture of acetone and methylene chloride and then dried. The granules are sized and mixed with 13.6% w/w of hydrogenated castor oil and 0.86% w/w of magnesium stearate.

Compression of tablets

Tablet (1)—1286 mg granules are pressed to tablet (equivalent to 1000 mg metformin hydrochloride) using 20.3×9.8 mm oval punches.

Tablet (2)—643 mg granules are pressed to tablet (equivalent to 500 mg metformin hydrochloride) using 14.95×8.35 mm oblong punches.

The dissolution rate of the novel dosage form was determined (Table 11)

TABLE 11

| Time | % Released | |
|---|---|---|
| (hour) | Tablet (1) | Tablet (2) |
| 1 | 50.3 | 52.5 |
| 2 | 70.5 | 74.2 |
| 4 | 88.0 | 89.4 |
| 6 | 100.9 | 100.7 |

Example 12

A) Micro matrix particles—93.02% w/w of metformin hydrochloride is mixed with 6.98% w/w of EUDRAGIT RS® (Ammonio Methacrylate Copolymer type B USP) and the mixture is granulated with a solvent mixture of acetone end methylene chloride and then dried. The granules are sized.

B) Coating of Micro matrix particles—90.56% w/w of micro matrix particles is charged in fluidized bed processor. 8.42% w/w of hydrogenated castor oil is dissolved in acetone and this coating solution is sprayed to coat the micro matrix particles. The coated micro matrix particles are sieved and mixed with 1.01% w/w magnesium stearate.

C) Compression of tablets 1187 mg granules are pressed to tablet (equivalent to 1000 mg metformin hydrochloride) using 20.3×9.8 mm oval punches.

The dissolution rate of the novel dosage form was determined (Table 12)

TABLE 12

| Dissolution profile | |
|---|---|
| Time (hour) | % Released |
| 1 | 37.59 |
| 2 | 48.91 |
| 4 | 59.24 |
| 6 | 74.85 |
| 8 | 86.15 |
| 10 | 88.48 |
| 12 | 93.30 |

Example 13

A) Micro matrix particles—Same as of example 12.

B) Coating of Micro matrix particles—88.70% w/w of micro matrix particles is charged in fluidized bed processor. 10.31% w/w of hydrogenated castor oil is dissolved in acetone and this coating solution is sprayed to coat the micro matrix particles. The coated micro matrix particles are sieved and mixed with 0.99% w/w magnesium stearate.

C) Compression of tablets 1212 mg granules are pressed to tablet (equivalent to 1000 mg metformin hydrochloride) using 20.3×9.8 mm oval punches.

The dissolution rate of the novel dosage form was determined (Table 13)

TABLE 13

| Dissolution profile | |
|---|---|
| Time (hour) | % Released |
| 1 | 31.84 |
| 2 | 44.66 |
| 4 | 50.55 |
| 6 | 65.29 |
| 8 | 73.29 |
| 10 | 79.80 |
| 12 | 85.90 |

Example 14

A) Micro matrix particles—Same as of example 12.

B) Coating of Micro matrix particles—92.51% w/w of micro matrix particles is charged in fluidized bed processor. 6.45% w/w of hydrogenated castor oil is dissolved in acetone and this coating solution is sprayed to coat the micro matrix particles. The coated micro matrix particles are sieved and mixed with 1.03% w/w magnesium stearate.

C) Compression of tablets 1162 mg granules are pressed to tablet (equivalent to 1000 mg metformin hydrochloride) using 20.3×9.8 mm oval punches.

The dissolution rate of the novel dosage form was determined (Table 14)

TABLE 14

| Dissolution profile | |
|---|---|
| Time (hour) | % Released |
| 1 | 45.90 |
| 2 | 60.10 |
| 4 | 77.00 |
| 6 | 89.70 |
| 8 | 96.72 |
| 10 | 98.57 |
| 12 | 104.33 |

Example 15

A) Micro matrix particles—Same as of example 12.

B) Coating of Micro matrix particles—91.33% w/w of micro matrix particles is charged in fluidized bed processor. 7.65% w/w of hydrogenated castor oil is dissolved in acetone and this coating solution is sprayed to coat the micro matrix particles. The coated micro matrix particles are sieved and mixed with 1.02% w/w magnesium stearate.

C) Compression of tablets 1177 mg granules are pressed to tablet (equivalent to 1000 mg metformin hydrochloride) using 20.3×9.8 mm oval punches.

The dissolution rate of the novel dosage form was determined (Table 15)

TABLE 15

Dissolution profile

| Time (hour) | % Released |
| --- | --- |
| 1 | 44.00 |
| 2 | 58.80 |
| 4 | 71.30 |
| 6 | 84.10 |
| 8 | 91.93 |
| 10 | 95.34 |
| 12 | 98.59 |

Example 16

Establishing the Pharmacokinetic Profile of Metformin Sustained Release Formulation The study was carried out to evaluate the pharmacokinetic parameters of the sustained release metformin formulation prepared as per the examples described above.

Methodology:

The biostudy had an open label, single period, single treatment, single dose study design. Non-compartmental Pharmacokinetic assessment was based on the plasma levels of metformin. Blood samples were obtained before dosing and at the following times after administration of test formulation;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Study Population:

Healthy male volunteers aged between 18 to 45 years.

Number of Subjects:

Four (04) volunteers were enrolled and all of them completed the study. All 04 volunteers were included in the Pharmacokinetic and safety analyses.

Test Formulation, Dose and Mode of Administration:

Test Formulation: 1000 mg Metformin sustained release (SR) formulation prepared as per the invention disclosed. Volunteers received a single oral dose of the above product with 200 ml of water 30 minutes after a following high calorie breakfast (~800 Kcal).

Pharmacokinetics:

The following Pharmacokinetic parameters were calculated using non compartments methods: the area under the drug plasma concentration curve from time of dosing to the time of last sampling point ($AUC_{(0-t)}$); the area under the drug plasma concentration versus time curve extrapolated to infinity ($AUC_{(0-Inf.)}$); the maximum measured concentration of the drug in the plasma ($C_{max}$) and the time at which this concentration was measured ($t_{max}$); the concentration at 24 hours ($C_{24h}$); the time taken for drug plasma concentration to decrease by 50% ($t_{1/2}$); and the terminal first-order elimination rate constant ($K_{el}$).

Area Under the curve (AUC) is the integral part of drug blood level over time from zero to infinity and is a measure of quantity of drug absorbed and in the body. AUC(0-t) represents area under the curve from zero to time t, where t represents the time at which last blood sample was taken.

$AUC_{(0-Inf)}$ represents area under the curve from zero to infinity.

Elimination half life of a drug is the time in hours necessary to reduce the drug concentration in the blood, plasma or serum to ½ after equilibrium is reached.

$C_{max}$ is the peak plasma concentration achieved after the administration of the drug.

$T_{max}$ is the time to reach peak plasma concentration.

Statistical Methods:

Descriptive statistics of relevant Pharmacokinetic parameters were performed.

Methods Used for Analysis of Metformin in Plasma Samples:

Estimation of Metformin in plasma samples was carried out by High Performance Liquid Chromatography and UV detection at 234 nm. Briefly 0.5 ml of plasma sample was precipitated with 2.0 ml acetonitrile. Samples were centrifuged and supernatant aliquot was washed with dichloromethane. After centrifugation, aqueous layer was injected on HPLC.

Figure 5:
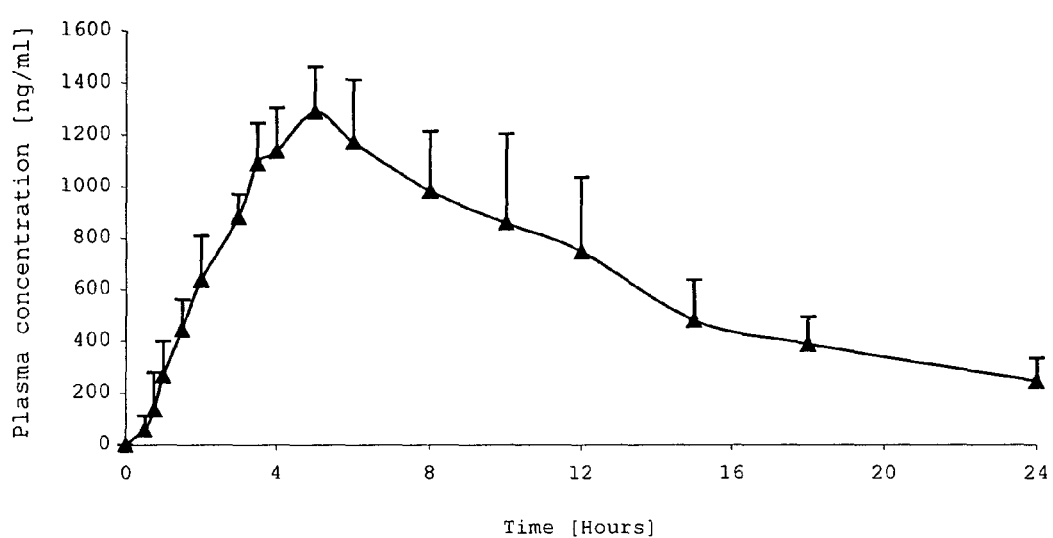
FIG. 5 is a plot of metformin plasma concentration versus time for formulation prepared as per the invention.

Pharmacokinetic Results:

The summary of the Pharmacokinetic parameters is contained in Table 16. The mean plasma concentration versus time curve is depicted in FIG. 5.

TABLE 16

Pharmacokinetic Parameters - Metformin SR (1000 mg)

| Parameters | Unit | Test (Mean ± SD) |
| --- | --- | --- |
| $AUC_{0-inf}$ | ng*hr/ml | 18776 ± 4672 |
| $AUC_{0-24}$ | ng*hr/ml | 15424 ± 3428 |
| $C_{max}$ | ng/ml | 1348 ± 116 |
| $C_{24h}$ | ng/ml | 245 ± 90 |
| $T_{max}$ | hr | 4.88 ± 1.03 |
| $T_{1/2}$ | hr | 9.28 ± 1.73 |

Conclusion:

Metformin has shown sustained release characteristics with following Pharmacokinetic profile;

The $AUC_{0-24}$ ranged from 12395 to 20345 ng*hr/ml.
The $AUC_{0-Inf}$ ranged from 15791 to 25727 ng*hr/ml.
The $C_{max}$ ranged from 1227 to 1452 ng/ml.
The $C_{24h}$ ranged from 165 to 373 ng/ml.
The $T_{max}$ ranged from 3.50 to 6.00 hours.
The $T_{1/2}$ ranged from 7.13 to 11.19 hours.

What is claimed is:

1. A modified release dosage form comprising of a high solubility active ingredient wherein the high solubility active ingredient has a solubility where less than 1 part to 30 parts of water is required to dissolve 1 part of active ingredient and said modified release dosage form is prepared by using a dual retard technique to control the release of the high solubility active ingredient, wherein said dual retard technique is a combination of matrix formulation and reservoir formulation said dosage form comprising a) micro matrix particles consisting of active ingredient(s) and hydrophobic release controlling agent wherein one or more hydrophobic release controlling agents are selected from the group consisting of ammonio methacrylate copolymers type A and B, methacrylic acid copolymer type A, B and C, poly(methyl methacrylate), poly(ethyl methacrylate), poly(butyl methacrylate), poly(isobutyl methacrylate), poly(hexyl methacrylate), poly(isodecyl methacrylate), poly lauryl methacrylate), poly (phenyl methacrylate), poly(methyl acrylate), poly(isopropyl acrylate), poly(isobutyl acrylate), poly(octadecyl acrylate), beeswax, carnauba wax, microcrystalline wax, ozokerite; cetostearyl alcohol, stearyl alcohol; cetyl alcohol myristyl alcohol; glyceryl monostearate glyceryl distearate; glycerol monooleate, acetylated monoglycerides, tristearin, tripalmitin, cetyl esters wax, glyceryl palmitostearate, glyceryl behenate hydrogenated castor oil and b)a coating of one or more of said hydrophobic release controlling agents on said micro matrix particles wherein the dosage form reduces the chances of burst effects.

2. A dosage form as claimed in claim 1, is in the form of tablet.

3. A dosage form according to claim 1, wherein said hydrophobic release controlling agents are selected from ammonio methacrylate co-polymers.

4. A dosage form according to claim 3, wherein ammonio methacrylate co-polymers are selected from the group consisting of Ammonio Methacrylate Copolymer type B, Ammonio Methacrylate Copolymer type A and Polyacrylate dispersion 30%.

5. A dosage form according to claim 1, wherein in micro matrix particles, the active ingredient and one or more hydrophobic release controlling agents are present in a ratio of from 100:2.5 to 100:30.

6. A dosage form according to claims 1-2, 3 or 4, wherein in micro matrix particles, the active ingredient can be less than or equal to 1500 mg.

7. A dosage form according to claim 1, wherein a coating of one or more hydrophobic release controlling agents on said micro matrix particles are selected from the group comprising of ammonio methacrylate copolymers type A and B, methacrylic acid copolymer type A, B and C, polyacrylate dispersion 30%, polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl acrylate), poly (octadecyl acrylate), beeswax, carnauba wax, microcrystalline wax, ozokerite; cetostearyl alcohol, stearyl alcohol; cetyl alcohol myristyl alcohol; glyceryl monostearate glycerol distearate; glycerol monooleate, acetylated monoglycerides, tristearin, tripalmitin, cetyl esters wax, glyceryl palmitostearate, glyceryl behenate hydrogenated castor oil.

8. A dosage form according to claim 7, wherein the hydrophobic release controlling agents are selected from glyceryl monostearate glycerol disterate, glycerol monooleate, acetylated monoglycerides, tristearin, tripalmitin, cetyl esters wax, glyceryl palmitostearate, glyceryl behenate and hydrogenated castor oil.

9. A dosage form according to claim 8, wherein the hydrophobic release controlling agents are selected from the group consisting of hydrogenated castor oil and glycerol disterate.

10. A dosage form according to claim 1, wherein micro matrix particles and coating of one or more hydrophobic release controlling agents are present in a ratio of from 100:2.5 to 100:30.

11. A dosage form according to claim 1, wherein the high solubility active ingredient is selected from the group consisting of antidiabetic agents, anti-histamines, anti-depressants, anti-viral agents, anesthetics, antacids, anti-arthritis, antibiotics, anti-psychotics, anti-spasmodics, anxiolytic agents, appetite suppressants, cardiovascular agents, cough suppressants, emollients, gastro-intestinal agents, growth regulators, respiratory stimulants, vitamins, angiotensin converting enzyme inhibitors, anti-asthmatics, anti-cholesterolemics, anti-convulsants, anti-depressants, anti-diarrhea preparations, anti-infective, anti-inflammatory agents, anti-nauseants, anti-stroke agents, anti-tumor drugs, anti-tussives, anti-uricemic drugs, amino-acid preparations, antiemetics; antiobesity drugs, antiparasitics, antipyretics, appetite stimulants, cerebral dilators, chelating agents, cholecystokinin antagonists, cognition activators, deodorants, dermatological agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors, vertigo agents, biguanides, sulphonylurease, meglitinides, PPAR gamma agonists and alpha-glucosidase inhibitors.

12. A dosage form according to claim 1, wherein the high solubility active ingredient is selected from the group consisting of metformin hydrochloride, phenformin, buformin, captopril, ranitidine hydrochloride, potassium chloride, clindamycin, hydroxyurea, erythromycin lactobionate, vancomycin hydrochloride; balsalazide disodium, aminocaproic acid, lisinopril, tramadol, acetaminophen, ciprofloxacin, esters of ampicillin, sodium valproate, niacin, diltiazem, venlafaxine, isosorbide 5-imononitrate, isosorbide dinitrate, pentoxyphylline, propranolol and quetiapine or pharmaceutically acceptable salts thereof.

13. A dosage form according to claim 1, for twice a day administration.

14. A dosage form according to claim 1, wherein the high solubility active ingredient is niacin.

15. A modified release dosage form according to claim 14, wherein the composition of the micro matrix particles and coated micro matrix particles is as follows--Micro matrix particles--Niacin 75% w/w to 99% w/w Ammonio Methacrylate Copolymer type B 1% w/w to 25% w/w Coated micro matrix particles Micro matrix particles 70% w/w to 99% w/w Hydrogenated castor oil 1% w/w to 30% w/w Magnesium stearate 0% w/w to 2% w/w.

16. A dosage form according to claim 1, wherein the high solubility active ingredient is sodium valproate.

17. A process for the preparation of a modified release dosage form comprising a) preparing a micro matrix particles consisting of high solubility active ingredient and one or more hydrophobic release controlling agent wherein the ratio of active ingredient(s) and hydrophobic release controlling agent is in the range of 100:2.5 to 100:30 and b) coating the said micro matrix particles consisting of high solubility active ingredient by one or more hydrophobic release controlling agent, wherein the ratio of micro-matrix particles and hydrophobic release controlling agent is in the range of 100:2.5 to 100:30.

18. A modified release dosage form comprising of a metformin hydrochloride prepared by using dual-retard technique to control the release of metformin,wherein said dual retard technique is a combination of matrix formulation and reservoir formulation said dosage form comprising a) micro matrix particles consisting of metformin hydrochloride and one or more hydrophobic release controlling agent wherein the ratio of metformin hydrochloride and hydrophobic release controlling agent is in the range of 100:2.5to 100:30 and b) coating of one or more hydrophobic release controlling agent on micro matrix particles, the ratio of micro-matrix particles and hydrophobic release controlling agent is in the range of 100:2.5 to 100:30wherein the dosage form reduces the chances of burst effects.

19. A dosage form as claimed in claim 18, is in the form of tablet.

20. A dosage form according to claim 18, wherein the hydrophobic release controlling agents employed for the micro matrix particles are selected from the group consisting of ammonio methacrylate copolymers type A and B, methacrylic acid copolymer type A, B and C, polyacrylate dispersion 30%, polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly (hexyl methacrylate), poly(isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate; glycerol monooleate, acetylated monoglycerides, tristearin, tripalmitin, cetyl esters wax, glyceryl palmitostearate, glyceryl behenate and hydrogenated castor oil.

21. A dosage form according to claim 20, wherein the hydrophobic release controlling agents are selected from ammonio methacrylate co-polymers.

22. A dosage form according to claim 21, wherein the ammonio methacrylate co-polymers are selected from the groups consisting of Ammonio Methacrylate Copolymer type B, Ammonio Methacrylate Copolymer type A and Polyacrylate dispersion 30%.

23. A dosage form according to one of claims 18-21, wherein in micro matrix particles, metformin hydrochloride can be less than or equal to 1500 mg.

24. A dosage form according to claim 18, wherein the coating of one or more hydrophobic release controlling agents on said micro matrix particles are selected from the group consisting ammonio methacrylate copolymers type A and B, methacrylic acid copolymer type A, B and C, polyacrylate dispersion 30%,polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl acrylate), poly (octadecyl acrylate), waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate; glycerol monooleate, acetylated monoglycerides, tristearin, tripalmitin, cetyl esters wax, glyceryl palmitostearate, glyceryl behenate and hydrogenated castor oil.

25. A dosage form according to claim 24, wherein the hydrophobic release controlling agents are selected from fatty acid esters.

26. A dosage form according to claim 25, wherein fatty acid ester is selected from the group consisting of hydrogenated castor oil and glycerol distearate.

27. A modified release dosage form according to claim 18, wherein the composition of the micro matrix particles and coated micro matrix particles is as follows-Micro matrix particles--Metformin hydrochloride 75% w/w to 99% w/w;

Ammonio Methacrylate Co-polymer type B 1% w/w to 25% w/w Coated micro matrix particles;

Micro matrix particles 70% w/w to 99% w/w;

Hydrogenated castor oil 1% w/w to 30% w/w;

Magnesium stearate 0% w/w to 2% w/w.

28. A dosage form according to claim 18, is once a day oral formulation.

29. A dosage form as claimed in claim 1, wherein the said dosage form may optionally contain more than one high solubility active ingredient.

30. A dosage form as claimed in claim 18, wherein the said dosage form may optionally contain more than one antidiabetic active ingredient.

31. A process for the preparation of a modified release dosage form comprising a) preparing a micro matrix particles consisting of metformin hydrochloride and one or more hydrophobic release controlling agent(s) wherein the ratio of metformin hydrochloride and hydrophobic release controlling agent is in the range of 100:2.5 to 100:30 and b)coating the said micro matrix particles consisting of metformin hydrochloride by one or more hydrophobic release controlling agent, wherein the ratio of micro-matrix particles and hydrophobic release controlling agent is in the range of 100: 2.5 to 100:30.

32. A dosage form according to claim 1, for once a day administration.

* * * * *